(12) United States Patent
Hloucha et al.

(10) Patent No.: US 8,658,581 B2
(45) Date of Patent: *Feb. 25, 2014

(54) SHAMPOO COMPOSITION WITH IMPROVED CARE PERFORMANCE

(75) Inventors: Matthias Hloucha, Köln (DE); Hans-Martin Haake, Erkrath (DE); Esther Küsters, Düsseldorf (DE); Jasmin Menzer, Mannheim (DE); Wolf Eisfeld, Langenfeld (DE); Werner Seipel, Hilden (DE); Hermann Hensen, Haan (DE); Esther Ricarda Reinhardt, Bad Salzuflen (DE)

(73) Assignee: Cognis IP Management GmbH, Duesseldorf (DE)

( * ) Notice: Subject to any disclaimer, the term of this patent is extended or adjusted under 35 U.S.C. 154(b) by 37 days.

This patent is subject to a terminal disclaimer.

(21) Appl. No.: 12/678,381

(22) PCT Filed: Jun. 14, 2008

(86) PCT No.: PCT/EP2008/004803
§ 371 (c)(1),
(2), (4) Date: Aug. 26, 2010

(87) PCT Pub. No.: WO2008/155075
PCT Pub. Date: Dec. 24, 2008

(65) Prior Publication Data
US 2010/0311627 A1    Dec. 9, 2010

(30) Foreign Application Priority Data

Jun. 19, 2007 (EP) .................................... 07011967
Sep. 27, 2007 (DE) .......................... 10 2007 046 575
Apr. 3, 2008 (DE) .......................... 10 2008 017 032
Apr. 3, 2008 (DE) .......................... 10 2008 017 034
May 7, 2008 (DE) .......................... 10 2008 022 433
May 21, 2008 (DE) .......................... 10 2008 024 570

(51) Int. Cl.
| | | |
|---|---|---|
| *A61Q 5/02* | (2006.01) | |
| *A61K 8/18* | (2006.01) | |
| *A61K 8/30* | (2006.01) | |
| *A61K 8/73* | (2006.01) | |
| *C11D 17/00* | (2006.01) | |
| *C11D 3/20* | (2006.01) | |
| *C11D 3/22* | (2006.01) | |
| *C11D 1/12* | (2006.01) | |
| *C11D 1/62* | (2006.01) | |
| *C11D 1/90* | (2006.01) | |

(52) U.S. Cl.
USPC ........... 510/119; 510/121; 510/123; 510/124; 510/125; 510/127; 510/470; 510/495; 510/504; 510/506; 424/70.11; 424/70.13; 424/70.19; 424/70.21; 424/70.24

(58) Field of Classification Search
USPC .......... 510/119, 121, 123, 124, 125, 127, 470, 510/475, 495, 504, 506; 424/401, 70.11, 424/70.13, 70.19, 70.21, 70.24
See application file for complete search history.

(56) References Cited

U.S. PATENT DOCUMENTS

| | | | | |
|---|---|---|---|---|
| 4,885,158 A * | 12/1989 | Tracy et al. | ...................... | 424/69 |
| 4,957,731 A * | 9/1990 | Helioff et al. | ................... | 424/62 |
| 5,578,298 A * | 11/1996 | Berthiaume et al. | ...... | 424/70.122 |
| 5,980,874 A * | 11/1999 | Foerster et al. | ................. | 424/65 |
| 6,180,117 B1 * | 1/2001 | Berthiaume et al. | .......... | 424/401 |
| 6,284,230 B1 * | 9/2001 | Sako et al. | ................. | 424/70.11 |
| 7,087,560 B2 * | 8/2006 | McManus et al. | ............ | 510/119 |
| 7,754,667 B2 * | 7/2010 | Walters et al. | ................ | 510/127 |
| 7,901,772 B2 * | 3/2011 | Smets et al. | ................ | 428/402.2 |
| 2003/0086896 A1 * | 5/2003 | Midha et al. | ................ | 424/70.17 |
| 2004/0136940 A1 * | 7/2004 | Lazarowitz | ................. | 424/70.13 |
| 2005/0079193 A1 * | 4/2005 | Nieendick et al. | ............ | 424/401 |
| 2005/0142094 A1 * | 6/2005 | Kumar | ......................... | 424/70.14 |
| 2006/0039956 A1 * | 2/2006 | Hensen et al. | ................. | 424/443 |
| 2006/0089290 A1 * | 4/2006 | McManus et al. | ............ | 510/504 |
| 2006/0165639 A1 | 7/2006 | Gauweiler et al. | | |
| 2007/0027051 A1 * | 2/2007 | Staudigel et al. | ............ | 510/130 |
| 2007/0212320 A1 * | 9/2007 | Demitz et al. | ............. | 424/70.15 |
| 2008/0020057 A1 * | 1/2008 | Niebauer et al. | .............. | 424/502 |

FOREIGN PATENT DOCUMENTS

| | | |
|---|---|---|
| DE | 10241296 | 3/2004 |
| DE | 102004030885 | 2/2006 |
| WO | WO 99/32079 A1 * | 7/1999 |
| WO | 99/53889 | 10/1999 |
| WO | WO 2005/020938 A1 * | 3/2005 |
| WO | 2006000257 | 1/2006 |

OTHER PUBLICATIONS

International Search Report, PCT/EP2008/004803 dated Oct. 22, 2009.

* cited by examiner

*Primary Examiner* — Lorna M Douyon
(74) *Attorney, Agent, or Firm* — Servilla Whitney LLC

(57) ABSTRACT

A cosmetic preparation is disclosed, comprising (a) at least one surfactant selected from the group consisting of non-alkoxylated anionic surfactants, zwitterionic surfactants and amphoteric surfactants, (b) a microemulsion, and (c) at least one cationic polymer.

8 Claims, No Drawings

SHAMPOO COMPOSITION WITH IMPROVED CARE PERFORMANCE

CROSS REFERENCE TO RELATED APPLICATIONS

This application is the National Stage entry of PCT/EP2008/004803, filed Jun. 14, 2008, which claims priority to European Application number 07011967, filed Jun. 19, 2007; German Application number 102007046575.2, filed Sep. 27, 2007; German Application number 102008017032.1, filed Apr. 3, 2008; German Application number 102008017034.8; filed Apr. 3, 2008; German Application number 102008022433.2, filed May 7, 2008; and German Application number 102008024570.4, filed May 21, 2008; all of which are incorporated herein by reference in their entireties.

FIELD OF THE INVENTION

The invention is in the field of cosmetic compositions for conditioning skin and hair which comprise microemulsions and polymers.

BACKGROUND OF THE INVENTION

After washing, skin and hair often feel rough and brittle, particularly if they have already been damaged by environmental influences. Moreover, hair may also be damaged as a result of coloring or perming and can then, after washing, often be characterized by a dry strawlike feel.

Consequently, conditioners are often used in shampoo compositions which are intended to counteract these disadvantages. Shampoo compositions are therefore often found which comprise silicones as conditioners. However, these can irreversibly attach to the hair and thus for their part cause negative effects on the feel, in the worst case even lead to problems when coloring and perming hair.

Furthermore, oils and waxes are suitable as conditioning agents in these cosmetic preparations. However, these are by far not as marked in their effect as the aforementioned silicones. Moreover, as a result of using these conditioners, only cloudy formulations are possible, and these oils and waxes can in any case only be stabilized in small amounts in the preparations.

As a result of using alkoxylated surfactants, mostly alkyl ether sulfates, upon using the cosmetic compositions skin irritations may arise and, moreover, calls for "green cosmetics" which are free from alkoxylated compounds are increasing. For these limitations with regard to the surfactants, there has hitherto been no satisfactory solution for providing shampoos with a good conditioning performance.

The object of the present invention was therefore to provide cosmetic compositions, the conditioning performance of which corresponds to that of silicone-containing preparations, or at best even surpasses them, and which, while avoiding alkoxylated ingredients, have foaming properties which are at least equally as good as compositions based on alkoxylated ingredients.

Surprisingly, it has been found that a cosmetic preparation comprising (a) at least one surfactant selected from non-alkoxylated anionic, zwitterionic or amphoteric surfactants, (b) a microemulsion and (c) at least one cationic polymer achieves the object stated above.

DETAILED DESCRIPTION OF PREFERRED EMBODIMENTS

Incorporation of a microemulsion as component (b) of the preparations according to the invention permits the transparent and stable incorporation of relatively large amounts of oil bodies, which then, synergistically with the cationic polymers of component (c) in the composition stabilized by the surfactants of component (a), bring about the exceptional conditioning properties of the preparation.

Surfactants

As component a), nonalkoxylated anionic, zwitterionic or amphoteric surfactants may be present. Typical examples of anionic surfactants are soaps, alkyl-benzenesulfonates, alkanesulfonates, olefinsulfonates, α-methyl ester sulfonates, sulfo fatty acids, alkyl sulfates, monoglyceride sulfates, fatty acid amide sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, alkyl oligoglucoside carboxylates, protein fatty acid condensates (in particular wheat-based vegetable products) and alkyl phosphates. Typical examples of amphoteric or zwitterionic surfactants are alkylbetaines, alkylamidobetaines, aminopropionates, aminoglycinates, imidazoliniumbetaines and sulfobetaines. Preference is given to alkyl sulfate and particular preference is given to a combination of alkyl sulfate and cocamidopropylbetaine, and very particular preference is given to a combination of lauryl sulfate and cocamidopropylbetaine.

Microemulsion

The microemulsions of component c) preferably have an average particle size of less than 1 μm. Preference is given to using microemulsions based on alkyl polyglycosides as component (b) of the present invention.

These emulsions are prepared by firstly preparing, in a first step, a microemulsion comprising at least 10-20% by weight of an alkyl (oligo)glycoside of the general formula $R^1O\text{-}[G]_p$ in which $R^1$ is an alkyl and/or alkenyl radical having 4 to 22 carbon atoms, G is a sugar radical having 5 or 6 carbon atoms and p is numbers from 1 to 10, and 4-10% by weight of an ester of glycerol with a saturated or unsaturated fatty acid of chain length C12-C22, and 5-30% by weight of an oil body, and the remainder to 100% by weight, water.

Microemulsions are understood as meaning initially all macroscopically homogeneous, optically transparent, low viscosity and in particular thermodynamically stable mixtures of two immiscible liquids and at least one nonionic or one ionic surfactant. The average particle sizes of the microemulsions are usually below 100 nm, they have high transparency and are stable to a visible phase separation upon centrifugation at 2000 rpm for at least 30 minutes.

The microemulsions are preferably prepared simply by mixing the oil phase with the further oil-soluble ingredients, heating the oil phase to above the melting point of all of the constituents and then adding the aqueous surfactant-containing phase. The thermodynamically stable microemulsion is then formed spontaneously, it being necessary to stir a little as well.

The microemulsion comprises as obligatory constituents a sugar surfactant, specifically an alkyl (oligo)-glycoside (also referred to below as "APG"). Alkyl and/or alkenyl oligoglycosides within the context of the present teaching conform here to the formula $R^1O\text{-}[G]_p$ in which $R^1$ is an alkyl and/or alkenyl radical having 4 to 22 carbon atoms, G is a sugar radical having 5 or 6 carbon atoms and p is numbers from 1 to 10. They can be obtained by the relevant methods of preparative organic chemistry. The alkyl and/or alkenyl oligoglycosides can be derived from aldoses or ketoses having 5 or 6 carbon atoms, preferably glucose. The preferred alkyl and/or alkenyl oligoglycosides are thus alkyl and/or alkenyl oligoglucosides. The index number p in the general formula (I) gives the degree of oligomerization (DP), i.e. the distribution of mono- and oligoglycosides, and is a number between 1 and 10. Whereas p in a given compound must always be an integer and here in particular can assume the values p=1 to 6, the value p for a specific alkyl oligoglycoside is an analytically determined parameter which in most cases is a fraction. Preference is given to using alkyl and/or alkenyl oligoglycosides with an average degree of oligomerization p of from 1.1 to 3.0. From an application point of view, preference is given to those alkyl and/or alkenyl oligoglycosides whose degree of oligomerization is less than 1.7 and is in particular between 1.2 and 1.5. APGs are present in the microemulsions according to the present invention in amounts between 10 and 20% by weight, in each case based on the total amount of the microemulsion. Particular preference is given here to amounts in the range from 14 to 19% by weight.

Furthermore, esters of fatty acids of chain length C12-C22 with glycerol are present in the emulsions. Preference is given here to using monoesters of glycerol, monoesters of glycerol with unsaturated linear fatty acids in particular being suitable. Within the context of the invention, particular preference is given to glycerol monooleate. These glycerol esters are present in the microemulsions in amounts of from 4 to 10% by weight, preferably 5 to 9% by weight—in each case based on the total weight of the microemulsion.

Finally, the microemulsions also comprise an oil body, i.e. a non-water-soluble organic phase in amounts of from 5 to 30% by weight. Here, particularly preferred oil phases are selected from the group of Guerbet alcohols based on fatty alcohols having 6 to 18 carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, esters of linear $C_6$-$C_{22}$-fatty acids with branched alcohols, esters of $C_6$-$C_{22}$-fatty alcohols and/or Guerbet alcohols with aromatic carboxylic acids, triglycerides based on $C_6$-$C_{10}$-fatty acids, liquid mono-/di-/triglyceride mixtures based on $C_6$-$C_{18}$-fatty acids, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, Guerbet carbonates based on fatty alcohols having 6 to 18, preferably 8 to 10, carbon atoms, esters of benzoic acid with linear and/or branched $C_6$-$C_{22}$-alcohols, linear or branched, symmetrical or asymmetrical dialkyl ethers having 6 to 22 carbon atoms per alkyl group, silicone oils and/or aliphatic or naphthenic hydrocarbons, dialkyl-cyclohexanes and/or silicone oils. However, solid fats and/or waxes may also be used as oil component. These may also be present in a mixture with the oils specified in the previous section. Typical examples of fats are glycerides, i.e. solid or liquid vegetable or animal products which consist essentially of mixed glycerol esters of higher fatty acids. Here, mention should be made in particular of solid mono- and diglycerides, such as, for example, glycerol monooleate or glycerol monostearate. Suitable waxes are inter alia natural waxes, such as, for example, candelilla wax, carnauba wax, Japan wax, esparto grass wax, cork wax, guaruma wax, rice germ oil wax, sugar cane wax, ouricury wax, montan wax, beeswax, shellac wax, spermaceti, lanolin (wool wax), uropygial grease, ceresin, ozokerite (earth wax), petrolatum, paraffin waxes, microwaxes; chemically modified waxes (hard waxes), such as, for example, montan ester waxes, sasol waxes, hydrogenated jojoba waxes, and also synthetic waxes, such as, for example, polyalkylene waxes and polyethylene glycol waxes. Tocopherols and essential oils are likewise suitable as oil component.

Hydrocarbons is the term used to refer to organic compounds which consist only of carbon and hydrogen. They include both cyclic and acyclic (=aliphatic) compounds. They include both saturated and mono- or polyunsaturated compounds. The hydrocarbons may be linear or branched. Depending on the number of carbon atoms in the hydrocarbon, the hydrocarbons can be divided into uneven-numbered hydrocarbons (such as, for example, nonane, undecane, tridecane) or even-numbered hydrocarbons (such as, for example, octane, dodecane, tetradecane). Depending on the type of branching, the hydrocarbons can be divided into linear (=unbranched) or branched hydrocarbons. Saturated, aliphatic hydrocarbons are also referred to as paraffins.

"Hydrocarbon mixture" is understood as meaning mixtures of hydrocarbons which contain up to 10% by weight of substances which are not classed as hydrocarbons. The % by weight data of the linear C11 and linear C13 hydrocarbons refer in each case to the sum of the hydrocarbons present in the mixture. The non-hydrocarbons present up to 10% by weight are not taken into consideration for this calculation.

The substances which are not classed as hydrocarbons and which may be present in the hydrocarbon mixture up to 10% by weight, in particular up to 8% by weight, preferably up to 5% by weight, are, for example, fatty alcohols which remain in the hydrocarbon mixture as unreacted starting materials.

The term "CX-hydrocarbon" includes hydrocarbons with a C number of X, thus, for example, the term C11 hydrocarbon includes all hydrocarbons with a C number of 11.

Preference is given to hydrocarbon mixtures where the mixture comprises
(a) 50 to 90% by weight of linear C11 hydrocarbons, preferably n-undecane
(b) 10 to 50% by weight of linear C13 hydrocarbons, preferably n-tridecane
based on the sum of the hydrocarbons.

Furthermore, preference is given to a hydrocarbon mixture which comprises at least 2 different hydrocarbons whose carbon number differs by more than 1, where these 2 different hydrocarbons constitute at least 60% by weight, preferably at least 70% by weight—based on the sum of the hydrocarbons.

The term "2 different hydrocarbons" refers to hydrocarbons with a different C number.

This means if the hydrocarbon mixture contains a hydrocarbon with a C number of n (n=integer), then the mixture contains at least one further hydrocarbon with a C number greater than or equal to n+2 or less than or equal to n−2.

Preferably, n is an uneven number, in particular 7, 9, 11, 13, 15, 17, 19, 21 and/or 23.

Furthermore, as hydrocarbon, it is possible to use a hydrocarbon mixture which comprises $^{14}C$ isotopes and where the hydrocarbon mixture contains at least 2 different hydrocarbons whose C number differs by more than 1.

A further essential constituent of the microemulsions is water. The water should preferably be demineralized. The microemulsions comprise preferably up to 81% by weight of water. Preferred ranges are amounts from 30 to 80% by weight and in particular from 45 to 65% by weight of water.

Besides the ingredients described above, the microemulsions can also comprise, as additional constituent, fatty alcohols of the general formula $R^2$—OH, where $R^2$ is a saturated or unsaturated, branched or unbranched alkyl or alkenyl radical having 6 to 22 carbon atoms. Typical examples are caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol, and technical-grade mixtures thereof which are produced, for example, during the high-pressure hydrogenation of technical-grade methyl esters based on fats and oils or aldehydes from the Roelen oxo synthesis, and also as monomer fraction in the dimerization of unsaturated fatty alcohols. Preference is given to technical-grade fatty alcohols having 12 to 18 carbon atoms, such as, for example, coconut, palm, palm kernel or tallow fatty alcohol. Particular preference is given to the co-use of cetyl alcohol, stearyl alcohol, arachyl alcohol and behenyl alcohol, and also mixtures thereof.

If fatty alcohols are present, they are preferably used in amounts up to 15% by weight, based on the total microemulsion, where the range from 1 to 10% by weight and preferably 2 to 8% by weight may be particularly preferred. These fatty alcohols, which are water-insoluble organic constituents, are also not covered by the definition of the oil body according to the invention.

The microemulsion which is prepared in the first step of the process according to the invention can furthermore also comprise anionic surfactants. Typical examples of anionic surfactants are soaps, alkyl-benzenesulfonates, alkanesulfonates, olefinsulfonates, α-methyl ester sulfonates, sulfo fatty acids, alkyl sulfates, mono- and dialkyl sulfosuccinates, mono- and dialkyl sulfosuccinamates, sulfotriglycerides, monoglyceride sulfates, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates and protein fatty acid condensates (in particular wheat-based vegetable products).

The microemulsions used in the process according to the invention can also comprise further nonionic, amphoteric and/or cationic surfactants, preferably in amounts of in total 1 to 25% by weight, based on the total weight of the emulsion. Typical examples of further nonionic surfactants (besides the alkyl (oligo)glycosides) are, for example, fatty acid N-alkylglucamides, polyol fatty acid esters, sugar esters, sorbitan esters, polysorbates, alcohol ethoxylates and amine oxides.

Examples of suitable amphoteric or zwitterionic surfactants are alkylbetaines, alkylamidobetaines, aminopropionates, aminoglycinates, imidazoliniumbetaines and sulfobetaines. Examples of suitable alkylbetaines are the carboxyalkylation products of secondary and in particular tertiary amines. Typical examples are the carboxymethylation products of hexylmethylamine, hexyldimethylamine, octyldimethylamine, decyldimethylamine, dodecylmethylamine, dodecyldimethylamine, dodecylethylmethylamine, $C_{12/14}$-cocoalkyldimethylamine, myristyldimethylamine, cetyl-dimethylamine, stearyldimethylamine, stearylethylmethylamine, oleyldimethylamine, $C_{16/18}$-tallow-alkyldimethylamine, and technical-grade mixtures thereof. Furthermore, carboxyalkylation products of amidoamines are also suitable. Typical examples are reaction products of fatty acids having 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselinic acid, linoleic acid, linolenic acid, elaeostearic acid, arachic acid, gadoleic acid, behenic acid and erucic acid, and also technical-grade mixtures thereof, with N,N-dimethylaminoethylamine, N,N-dimethylaminopropylamine, N,N-diethylaminoethylamine and N,N-diethylaminopropylamine which are condensed with sodium chloroacetate. Preference is given to the use of a condensation product of $C_{8/18}$-coconut fatty acid N,N-dimethylaminopropylamide with sodium chloroacetate. Furthermore, imidazoliniumbetaines are also suitable. These substances are also known substances which can be obtained, for example, by cyclizing condensation of 1 or 2 mol of fatty acid with polyfunctional amines, such as, for example, aminoethylethanolamine (AEEA) or diethylenetriamine. The corresponding carboxyalkylation products are mixtures of different open-chain betaines. Typical examples are condensation products of the aforementioned fatty acids with AEEA, preferably imidazolines based on lauric acid or in turn $C_{12/14}$-coconut fatty acid, which are then betainized with sodium chloroacetate.

Typical examples of cationic surfactants are quaternary ammonium compounds and ester quats, in particular quaternized fatty acid trialkanolamine ester salts.

Particularly preferred microemulsions have the following composition:

| | |
|---|---|
| alkyl (oligo)glycosides | 10 to 20% by weight |
| glycerol fatty acid esters | 4 to 10% by weight |
| oil bodies | 5 to 30% by weight |

The remainder to 100% by weight is then in each case water, if appropriate supplemented by further optional ingredients.

Cationic Polymers

As component b), the cosmetic compositions of the present patent application comprise cationic polymers. These are preferably selected from the group of homopolymers or copolymers of ester or amide derivatives of acrylic acid or methacrylic acid (e.g. INCI: Polyquaternium-7), homopolymers of methacryloylethyltrimethylammonium chloride (INCI: Polyquaternium-37), quaternary copolymers of hydroxyethylcellulose and diallyldimethylammonium chloride (INCI: Polyquaternium-4), polymeric quaternized ammonium salts of hydroxyethylcellulose which have been modified with a trimethylammonium-substituted epoxide (INCI: Polyquaternium-10, Polyquaternium-67), depolymerized guar gum derivatives which have been quaternized (INCI: Guar Hydroxypropyl Trimonium Chloride), amphoteric copolymers (INCI: Polyquaternium-74) or quaternized guar derivatives and quaternary copolymers of hydroxyethylcellulose and diallyldimethylammonium chloride. In one preferred embodiment, the cationic polymer (c) is selected from the group which is formed by polyquaternium-7, polyquaternium-10 and cationic guar derivatives. In one particularly preferred embodiment, preference is given to cationic guar derivatives since these correspond to the "green" concept. The preparations according to the invention preferably comprise 0.05 to 2% by weight of these cationic polymers.

Preference is given to a cosmetic preparation comprising
(a) alkyl sulfates and cocamidopropylbetaine,
(b) a microemulsion comprising
(b1) alkyl oligoglycosides,
(b2) esters of glycerol with a saturated or unsaturated fatty acid of chain length C12-22 and
(b3) oil bodies and
(b4) water, and
(c) a cationic polymer selected from the group which is formed by polyquaternium-7, polyquaternium-10 and cationic guar derivatives.

Particular preference is given to a cosmetic preparation comprising
(a) 5-20% by weight, based on the total composition, of alkyl sulfates and cocamidopropylbetaine, (b) 0.5-10% by weight, based on the total composition, of a microemulsion comprising (quantitative data for components (b1) to (b4) based on the microemulsion)
(b1) 10-20% by weight of alkyl oligoglycosides,
(b2) 4-10% by weight of esters of glycerol with a saturated or unsaturated fatty acid of chain length C12-22,
(b3) 5-30% by weight of an oil body and
(b4) remainder to 100% by weight water, and
(c) 0.05-1% by weight, based on the total composition of a cationic polymer selected from the group which is formed by polyquaternium-7, polyquaternium-10 and cationic guar derivatives.

The present invention further provides a process for preparing a cosmetic preparation by stirring (a) at least one surfactant selected from nonalkoxylated anionic, zwitterionic or amphoteric surfactants,
(b) a microemulsion and
(c) at least one cationic polymer with further cosmetic base substances.

EXAMPLES

Firstly, a microemulsion with the following composition was prepared by mixing the ingredients (tables 1 and 2):

TABLE 1

Composition of a microemulsion according to component b) of the invention:

| Substance | INCI | % by wt. of active substance |
| --- | --- | --- |
| Plantacare ® 2000 UP | Decyl Glucoside | 17.5 |
| Monomuls ® 90 O 18 | Glyceryl Oleate | 8 |
| Cetiol ® OE | Dicaprylyl Ether | 20 |
| Aqua dem. | | ad 100 |

TABLE 2

Shampoo formulations and performance during wet combing work

| Substance | INCI | % by wt. of active substance | | | |
| --- | --- | --- | --- | --- | --- |
| Sulfopon ® 1216G | Sodium C12-16 fatty alcohol sulfate | 4.8 | 4.8 | — | — |
| Texapon ® ALS Benz | Ammonium Lauryl Sulfate | — | — | 5.3 | 5.3 |
| Plantacare ® 2000 UP | Decyl Glucoside | 8.1 | 8.1 | — | — |
| Plantapon ® LGC Sorb | Sodium Lauryl Glucose Carboxylate (and) Lauryl Glucoside | — | — | 2.7 | 2.7 |
| Dehyton ® PK 45 | Cocamidopropyl Betaine | 2.1 | 2.1 | 3.1 | 3.1 |
| Emulsion as in table 1 | | — | 7.0 | — | 18.0 |
| Jaguar ® C 162 | Hydroxypropyl Guar Hydroxypropyl trimonium Chloride | 0.2 | 0.2 | 0.2 | 0.2 |
| Keltrol ® CG-SFT | Xanthan Gum | 1.0 | 1.0 | 1.0 | 1.0 |
| Sodium Benzoate | Sodium Benzoate | 0.5 | 0.5 | 0.5 | 0.5 |
| Citric Acid 50% (pH 5) | Citric Acid | q.s. | q.s. | q.s. | q.s. |
| Aqua dem. | | ad 100 | | | |
| Residual combing work [%] | | 100 | 56 | 100 | 39 |

The investigations with regard to the conditioning performance of the shampoos were carried out in each case on 10 hair tresses in an automated system for determining wet combing work.

The pretreatment of the hair tresses (12 cm/1 g) from IHIP was carried out in an automated hair treatment system:

30 min cleaning with 6% sodium lauryl ether sulfate, pH 6.5, then intensive rinsing of the hair 20 min bleaching with a solution of 5% hydrogen peroxide, pH 9.4 (adjusted with ammonium hydroxide solution), then intensive rinsing of the hair 30 min drying in a stream of air at 68° C.

Directly prior to the zero measurement, the hair was swollen in water for 30 minutes and then rinsed using an automatic wet combing-out apparatus for 1 minute. In the automated system for determining the wet and dry combing work, the combing forces were determined during combings and the combing work was calculated by integrating the measured force-displacement curves. Following the zero measurement, the hair was immediately treated with the formulation (0.25 g/g of hair). After a contact time of 5 minutes, rinsing was carried out using the automatic wet combing-out apparatus under standard conditions (38° C., 1 l/minute).

The treatment and the subsequent rinsing were repeated a second time. The comparison measurement (to the zero measurement) was then carried out. The measurements were carried out using the fine comb side of natural rubber combs. The residual combing work per tress was calculated as follows:

> Residual combing work=combing work after product treatment/combing work before product treatment Then, via the quotients of all 10 tresses, the mean and the standard deviation were determined.

What is claimed is:

1. A shampoo composition comprising:
    (a) one or more non-alkoxylated anionic surfactants,
    (b) 0.5-18% by weight, based on the total composition, of a microemulsion comprising, based on the microemulsion: 10-20% by weight decyl glucoside, 4-10% by weight glyceryl oleate, and 5-30% by weight dicaprylyl ether, and
    (c) 0.05-2% by weight, based on the total composition, of a cationic polymer selected from the group consisting of polyquaternium-10, cationic guar derivatives, and mixtures thereof;
    wherein the composition does not contain silicones and alkoxylated surfactants.

2. The composition of claim 1, wherein component (a) comprises an alkyl sulfate, a sulfonate, or a mixture of an alkyl sulfate and cocamidopropylbetaine.

3. The composition of claim 1 comprising:
    (a) 5-20% by weight, based on the total composition, of alkyl sulfates and cocamidopropylbetaine;
    (b) 0.5-10% by weight, based on the total composition, of the microemulsion; and
    (c) 0.05-1% by weight, based on the total composition of the cationic polymer.

4. The composition of claim 1, wherein the surfactant further comprises an amphoteric or zwitterionic surfactant.

5. The composition of claim 4, wherein the amphoteric surfactant is cocoamidopropyl betaine.

6. The composition of claim 1, wherein the cationic guar derivative is hydroxypropyl guar hydroxypropyltrimonium chloride.

7. The composition of claim 1, wherein the surfactant consists essentially of a non-alkoxylated sulfate surfactant or a non-alkoxylated sulfonate surfactant.

8. A process for preparing a shampoo composition according to claim 1 comprising:
    (1) stirring together the surfactants, microemulsion and cationic polymer, and
    (2) adding one or more additional shampoo base components.

* * * * *

UNITED STATES PATENT AND TRADEMARK OFFICE
CERTIFICATE OF CORRECTION

PATENT NO. : 8,658,581 B2  
APPLICATION NO. : 12/678381  
DATED : February 25, 2014  
INVENTOR(S) : Hloucha et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 186 days.

Signed and Sealed this
Eleventh Day of August, 2015

Michelle K. Lee
*Director of the United States Patent and Trademark Office*